US012788441B2

(12) United States Patent
Poulter

(10) Patent No.: US 12,788,441 B2
(45) Date of Patent: Nov. 10, 2026

(54) SPINAL IMPLANT SYSTEM AND METHOD

(71) Applicant: Gregory Poulter, Zionsville, IN (US)

(72) Inventor: Gregory Poulter, Zionsville, IN (US)

( * ) Notice: Subject to any disclaimer, the term of this patent is extended or adjusted under 35 U.S.C. 154(b) by 441 days.

(21) Appl. No.: 18/312,681

(22) Filed: May 5, 2023

(65) Prior Publication Data

US 2024/0173052 A1 May 30, 2024

Related U.S. Application Data

(63) Continuation of application No. 16/806,059, filed on Mar. 2, 2020, now abandoned.

(60) Provisional application No. 62/914,424, filed on Oct. 12, 2019, provisional application No. 62/815,669, filed on Mar. 8, 2019.

(51) Int. Cl.
*A61B 17/88* (2006.01)
*A61B 17/70* (2006.01)

(52) U.S. Cl.
CPC ...... *A61B 17/7013* (2013.01); *A61B 17/7032* (2013.01)

(58) Field of Classification Search
CPC ............ A61B 17/7011; A61B 17/7013; A61B 17/7032
USPC ......................... 606/264, 265, 270, 305, 308
See application file for complete search history.

(56) References Cited

U.S. PATENT DOCUMENTS

| | | | | |
|---|---|---|---|---|
| 5,545,165 A * | 8/1996 | Biedermann | A61B 17/7032 | 606/276 |
| 5,863,293 A * | 1/1999 | Richelsoph | A61B 17/7032 | 606/279 |
| 6,224,596 B1 * | 5/2001 | Jackson | A61B 17/7032 | 606/301 |
| 10,603,083 B1 * | 3/2020 | Gladieux | A61B 17/7002 | |
| 2004/0181224 A1* | 9/2004 | Biedermann | A61B 17/7037 | 606/279 |
| 2006/0195098 A1* | 8/2006 | Schumacher | A61B 17/7037 | 606/328 |
| 2010/0004693 A1* | 1/2010 | Miller | A61B 17/7001 | 606/301 |
| 2010/0145394 A1* | 6/2010 | Harvey | A61B 17/7032 | 606/305 |
| 2012/0041490 A1* | 2/2012 | Jacob | A61B 17/7032 | 606/279 |
| 2012/0303063 A1* | 11/2012 | Cahill | A61B 17/7041 | 606/267 |
| 2014/0094858 A1* | 4/2014 | Picetti | A61B 17/7037 | 606/308 |
| 2014/0180347 A1* | 6/2014 | Konieczynski | A61B 17/7037 | 606/306 |
| 2015/0282842 A1* | 10/2015 | Beyar | A61B 17/7049 | 606/273 |
| 2019/0038320 A1* | 2/2019 | Biedermann | A61B 17/7032 | |
| 2020/0281629 A1* | 9/2020 | Poulter | A61B 17/7013 | |

* cited by examiner

*Primary Examiner* — Eduardo C Robert
*Assistant Examiner* — David C Comstock
(74) *Attorney, Agent, or Firm* — Maginot, Moore & Beck, LLP

(57) ABSTRACT

A spinal construct is based on a fixed contour rod and modified bone screws configured to account for different height and angular offsets between the rod and the spinal anatomy. The rod contour is adapted for percutaneous introduction thereby eliminating the need for open spinal surgery for multi-level constructs.

2 Claims, 6 Drawing Sheets

SPINAL IMPLANT SYSTEM AND METHOD

PRIORITY CLAIM

This application claims priority to pending application Ser. No. 16/806,059, filed on Mar. 2, 2020, which is a utility filing from and claims priority to U.S. Provisional No. 62/815,669, filed on Mar. 8, 2019, and to U.S. Provisional No. 62/914,424, filed on Oct. 12, 2019. The disclosures of both provisionals, along with the appendices filed with the provisional applications, are incorporated herein by reference.

BACKGROUND

Spinal surgery and spinal implants have advanced considerably over the last half-century, resulting in an increased number of fusion surgeries performed each year. The current generation of spinal implants and procedures are designed to allow the safe application of spinal fixation with a great amount of customization to accommodate significant patient to patient variation in anatomy and alignment. However, in some respects, the flexibility allowed by current designs sacrifices the ability of these implants to control spinal alignment. In fusion surgery, achieving the correct spinal alignment is critical to achieve improved patient outcomes. The current state of the art use of rod and screw constructs to control spinal alignment involves one of two techniques. The first involves placing rods that are contoured to the patient's spine and then manipulating the rods by bending them or compressing/distracting on screws to effect alignment. The other technique involves creating rods from a preoperative plan that are custom shaped to the patient's desired alignment and then bringing the patients spine into alignment by reducing the screws to the rods in surgery.

The first minimally invasive surgeries were generally limited to discectomies and fusions at one or two vertebral levels. Rod fixation for correcting spinal deformities were more problematic for minimally invasive techniques due to the need to introduce a long, curved rod spanning multiple vertebral levels. Early techniques were developed for minimally invasive lumbar fixation using shorter curved rods that can easily be placed over a short segment of the spine. Attempts to expand these minimally invasive techniques to larger fusions has been limited as the geometry of the human spine necessitates a rod contour that cannot be introduced using a minimally invasive technique. To date, current rods, whether they are hand bent or pre-contoured, are designed to match the desired spinal curvature and thus are limited in their application of minimally invasive surgery.

Instrumentation for minimally invasive fusion systems include modifications of the standard pedicle screws and rods that allow them to be placed through small incisions in the skin. Placing a connecting rod through the tops of the screws requires that the screws line up with the shape of the rod that is being placed. This requirement for precise alignment has limited the application of minimally invasive techniques to fusions of only a small number of levels. In recent years, computer aided pre-surgical planning systems have allowed greater precision. This precision stems from the ability to develop a detailed pre operative plan and the ability to precisely place the implants according to that plan. This technology has expanded the capabilities of both standard and minimally invasive techniques by allowing the minimally invasive placement of screws and rods from the lower thoracic spine, across the lumbar spine to the pelvis. Even though the pre-surgical planning systems have addressed one of the primary limitations of minimally invasive deformity surgery, the current procedures are still limited by the curved shape of the rod.

In a typical procedure, the rod is pre-shaped or is manually bent at the time of surgery to a lordotic curve that matches the desired lordotic shape of the spine. This, however, can create extreme difficulty in placing the rod, particularly for correcting an extremely deformed spine. Another problem is that bending the spinal rod inherently weakens the rod to some degree at the bend points. A further difficulty arises from a rod bent to a lordosis matching the spine in which the rod is too curved to pass easily through the soft tissue of the patient when attempting to perform procedures spanning several vertebral levels. In cases that include fusions of multiple levels, particularly those spanning the lower lumbar spine, a minimally invasive insertion of the rods is not possible and necessitates an opening of the spine with a large incision. Although pre-planning screw and rod placements and advances in rod bending techniques have greatly improved spinal surgery, there is still a significant need for a spinal construct and surgical technique that can overcome the detriments noted above.

SUMMARY OF THE DISCLOSURE

The technology of the present disclosure differs substantially from the preexisting techniques as it involves using rods that are of standard dimensions and controlling the shape of the spine by controlling the relationship between the spine and rods by a combination of screw placement and angular control of the spine with implants that are rigid in the sagittal plane. This technique first involves creating a computerized 3-dimensional model of spines desired shape. Then preexisting rods are added to the model of the spine. The variation between the two is bridged by precise screw placement. This technique works for longer fusion constructs of multiple levels. Shorter constructs require the screws and rods to interact with each other at precise angles to establish the desired angular relationships. This requires the use of implants that are constrained in the sagittal plane to control the sagittal alignment for short constructs. Larger constructs may have their alignment controlled both by a combination of screws placement as well as fixed angular relationships between the rods and screws.

One difference between the method disclosed herein and current techniques is that the proposed system uses rods of a predefined shape and plans the screw depth and angular relationship to the rods. The goals of the system are to provide control of the patient's spinal alignment in fusion surgery for both long and short fusion constructs utilizing standardized (not patient specific implants) in both minimally invasive and open applications. Current rod/screw constructs are also limited in their application of minimally invasive surgery in long constructs that span the lumbar spine.

Accordingly, in one aspect of the disclosure, a bone screw for fixation in a vertebral body of a spine is provided that comprises an elongated shank having bone engaging threads and defining a longitudinal axis, and a rod-engaging portion connected to one end of the elongated shank. The rod-engaging portion defines a channel for receiving a spinal rod therein, wherein the channel is defined at a non-perpendicular angle relative to the longitudinal axis of the shank. In particular, the channel can be defined at an angle of between 5° and 45°. A kit can be provided that includes a plurality of such screws with different non-perpendicular angle so that the surgeon can select an optimum screw for a particular vertebral level.

In another aspect, another bone screw for fixation in a vertebral body of a spine includes a rod-engaging portion that is connected to the elongated shank so that the longitudinal axis of the shank is not colinear with a vertical axis through the rod-engaging portion. In particular, the longitudinal axis can be oriented at an angle relative to the vertical axis of between 5° and 45°. A kit can be provided that includes a plurality of such screws with different angles so that the surgeon can select an optimum screw for a particular vertebral level.

In another feature of the present disclosure, a bone screw for fixation in a vertebral body of a spine is provided that includes an elongated shank having bone engaging threads and defining a longitudinal axis, a rod-engaging portion defining a channel for receiving a spinal rod therein oriented perpendicular to the vertical axis, and an intermediate portion connecting the rod-engaging portion to the elongated shank. The intermediate portion has a height along the longitudinal axis of between 0.5 mm and 30 mm. A kit can be provided that includes a plurality of such screws, each having different heights so that the surgeon can select an optimum screw for a particular vertebral level.

The kits can include an elongated rod defining a fixed curved contour adapted for percutaneous introduction along a patient's spine. The fixed curved contour will ordinarily be offset from the patient's spine by different height and angular offsets at different vertebral levels. The surgeon can select among the screws described above to achieve coronal and sagittal correction of the patient's spine. The devices, kits and methods disclosed herein can be used for a wide range of spinal procedures and across any number of vertebral levels. Thus, while the present disclosure demonstrates the use of the devices, kits and methods in the correction of scoliosis, this disclosure is merely for illustrative purposes. The same devices, kits and methods can be used for shorter constructs, spanning only one or two vertebral levels.

DETAILED DESCRIPTION

Figure 1:
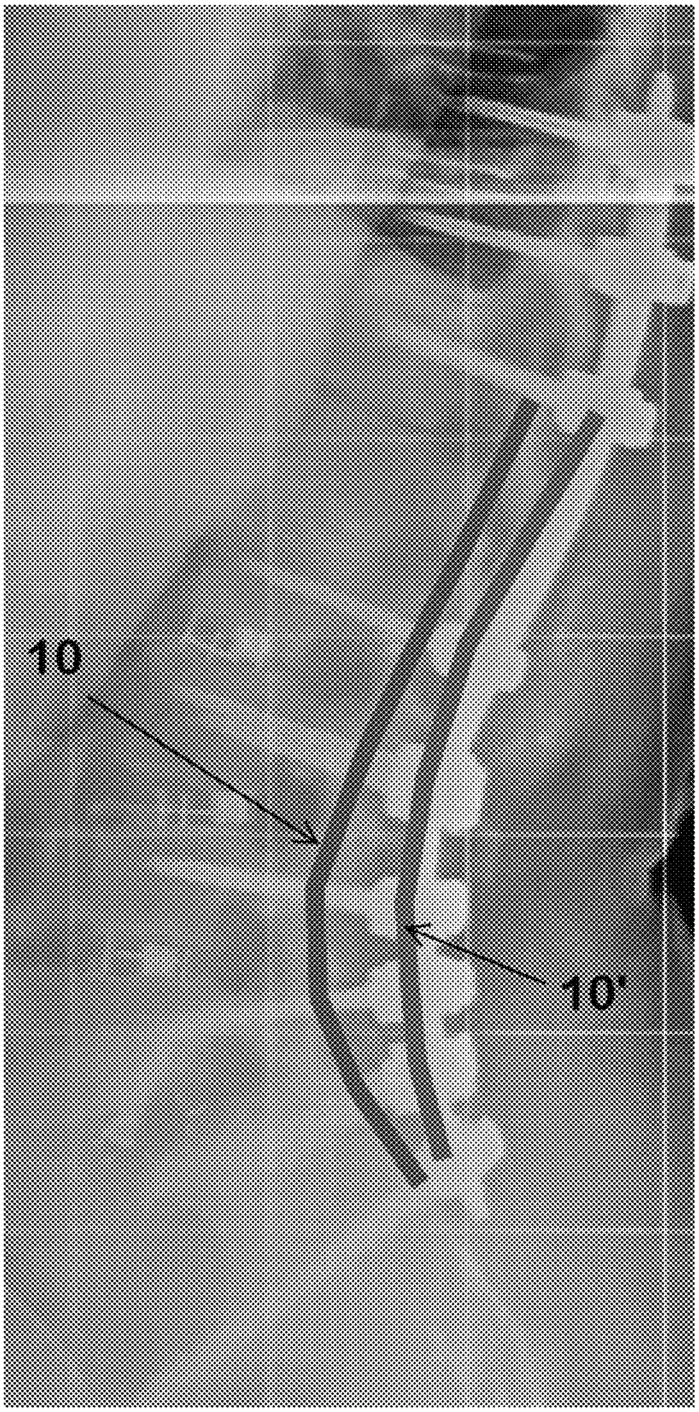
FIG. 1 is an X-ray image of a spine showing a conventional spinal rod for fixation and a modified rod according to the present disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

The present disclosure addresses these problems by providing a rod system incorporating a novel rod that has a lesser lordotic curve that can be easily passed under the tissues in a minimally invasive fashion. This concept of a rod designed to specifically allow minimally invasive placement in the treatment of long lumbar fusions is demonstrated by the rod 10' in the X-ray image of FIG. 1, as it is much less curved than the rod 10 that is representative of current rod shape strategies. As can be appreciated the conventional rod 10 has a significant curvature to match the patient's anatomy but this curvature prevents the rod from being placed in a minimally invasive fashion. It is noted that the rod 10' can be formed by conventional means, such as by bending, or can be formed in a 3D printing process akin to the UNID rod of Medicrea.

Figure 2:
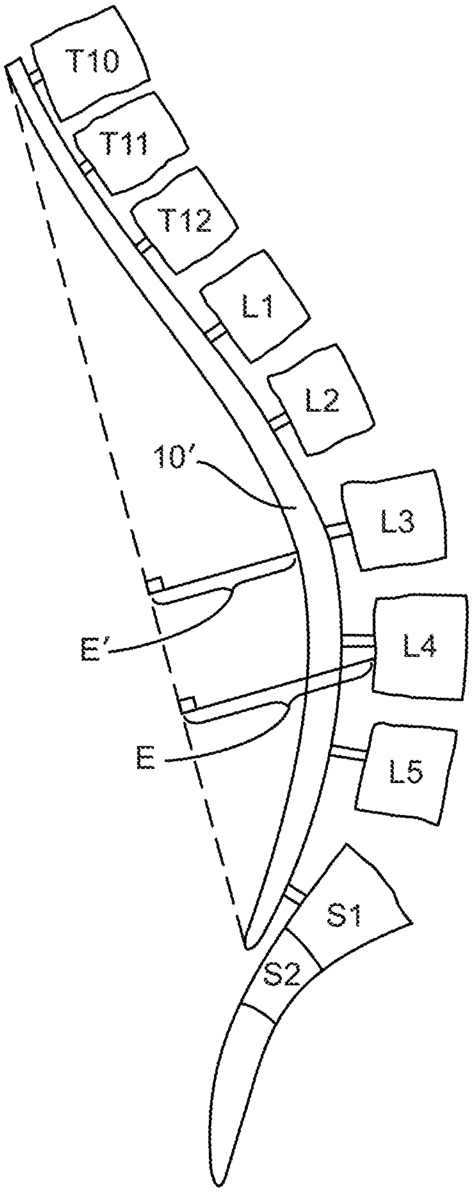
FIG. 2 is a representation of the spine in the sagittal plane showing the modified rod of the present disclosure.
Figure 3:
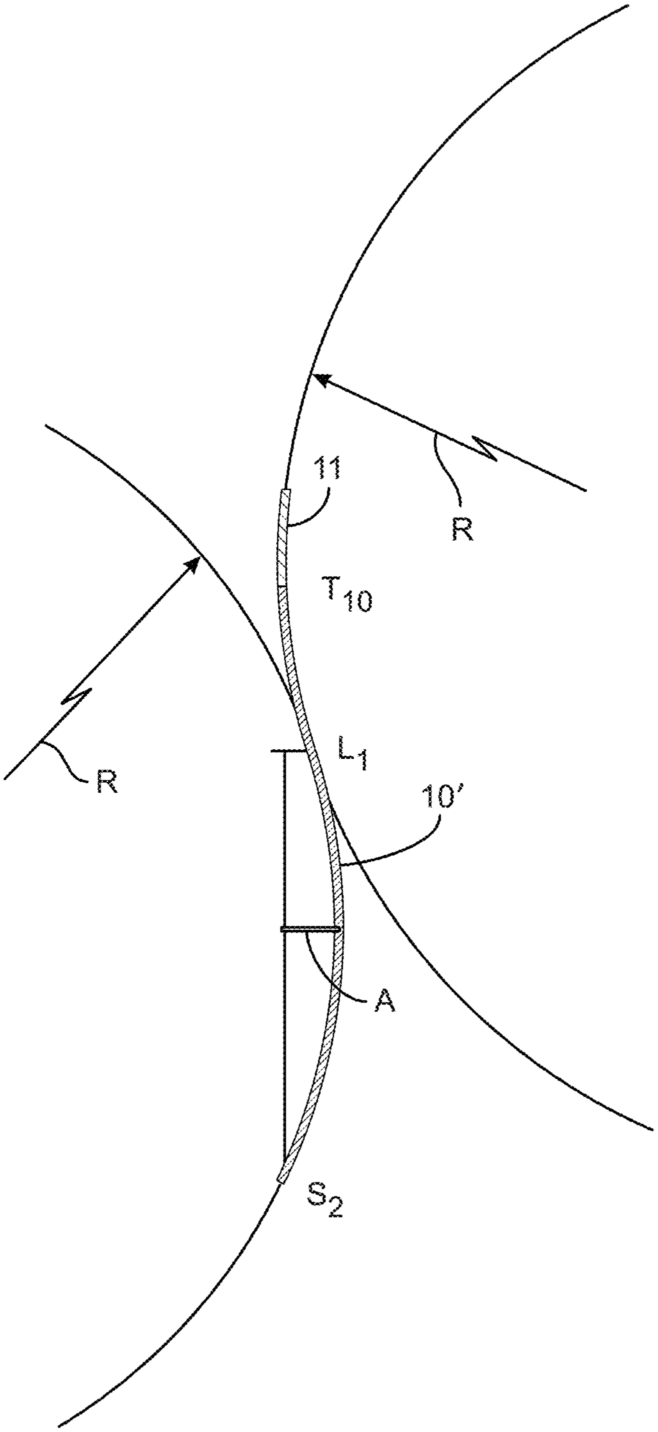
FIG. 3 is diagram of the curvature of the modified rod of the present disclosure.

The present disclosure provides devices and methods to accommodate the lesser curved pre-bent rod to the patient's anatomy. Thus, as depicted in FIG. 2, the method contemplates introducing a rod 10' having an excursion or offset E' or bend that is less than offset E of the patient's anatomy in order to facilitate, and achieve, percutaneous placement. A rod with reduced lumbar lordosis also has applications in open surgery as planning tulip screws that are proud of the bone surface can allow for control of spinal alignment. As shown in FIG. 2, the rod generally follows the thoracic vertebrae but begins to deviate from the surface of the lumbar vertebrae, finishing generally even (level) with the second sacral vertebra. The reduced curvature of the rod allows for subcutaneous cranial introduction. It can be appreciated that the rod 10' can be pre-bent or pre-formed into the reduced curvature configured shown in FIG. 2. More particularly, as illustrated in FIG. 3, the rod 10' can be sized to extend from S2 to T10. In this instance, the rod 10' includes two sections—caudal and cranial—each formed at a circular arc of radius R. The arc at the caudal portion provides the lordotic curvature and spans 60% of the total length of the rod from T10 to S2 (the T10-S2 length). The radius R is sized so that the anterior displacement A at the caudal (lordotic) portion is 9-11% of the total T10-S2 length of the rod. The rod 10' can include a cranial end portion 11 that can be trimmed and/or bent by hand as required for the particular patient anatomy. The end portion 11 can be provided with markings, such as laser etched markings, indicating the length from S2, to facilitate trimming the rod to the proper length. For instance, for a T10-S2 length of 45 cm, the anterior displacement A for the caudal (lumbar) portion is 4-5 cm and the length of the caudal portion (L1 to S2) is 27 cm. The radius R can be calculated using the equation: $((\text{L1-S2 length})^2/8\ A)+A/2$, so in the specific example, with A=5 cm, the radius R is 20.7 cm. It can be appreciated from the appearance of the rod 10' in FIG. 3 that the rod is well-suited to percutaneous introduction adjacent the vertebral levels to be instrumented. It should also be appreciated that a rod prepared and used according to the present disclosure does not need to span the seven vertebral levels of the rod 10' in the present example. The rod can be shorter or longer, depending on the desired treatment.

Figure 4:
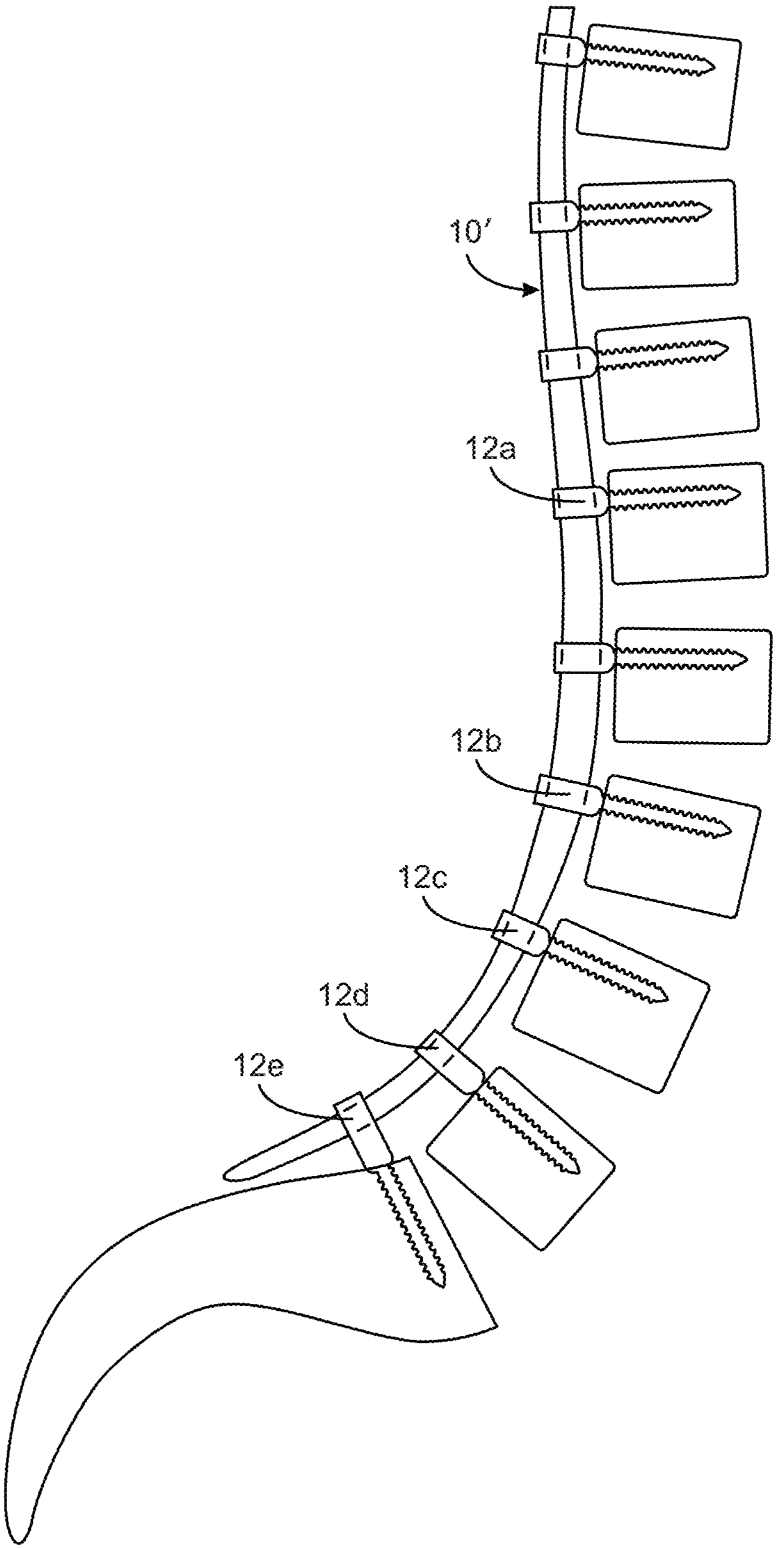
FIG. 4 is a representation of the spine in the sagittal plane with the modified rod and bone screws of the present disclosure.
Figure 5:
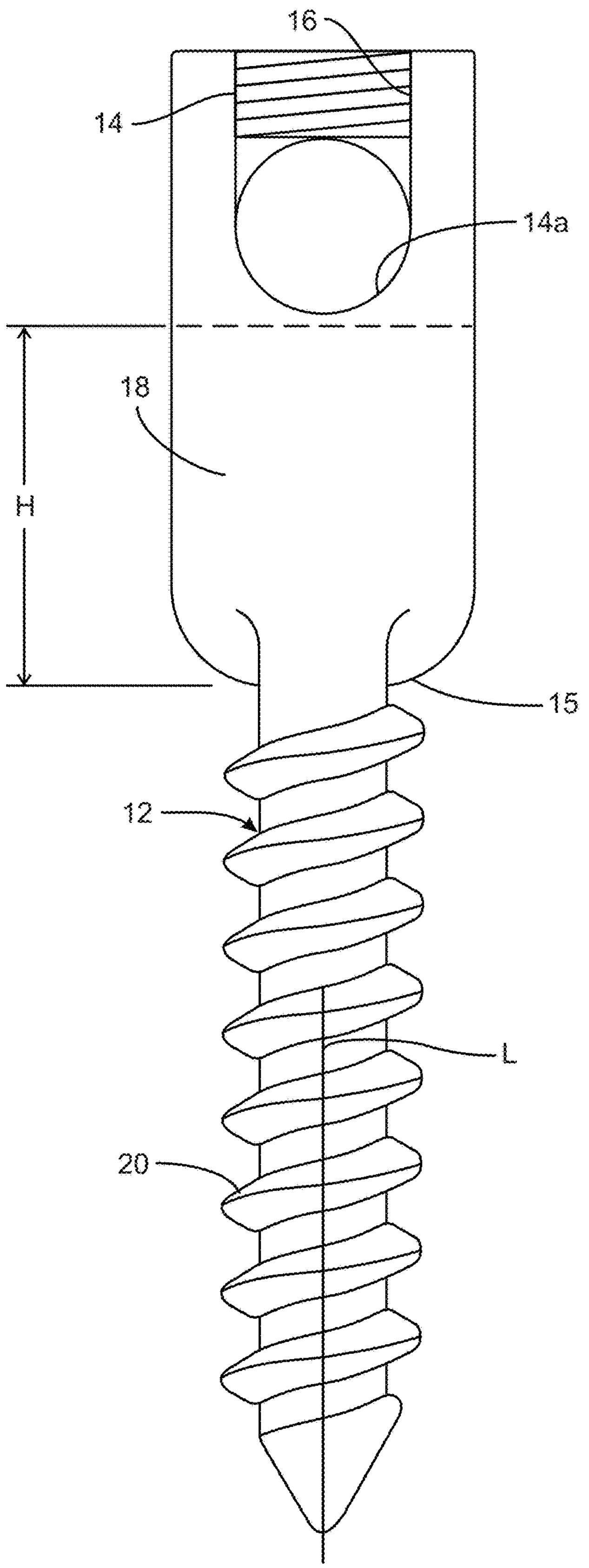
FIG. 5 is a view of a bone screw according to one aspect of the present disclosure.

When placing a rod with a decreased lordotic bend, there is a risk of inducing a flat back deformity in the patient's spinal alignment. To allow the lumbar spine to achieve a proper anterior offset and suitable lordotic angles, precise placement of the pedicle screws and a modified pedicle screw is provided according to the present disclosure. In particular, in order to accept the lesser curved spinal rod 10', the present disclose contemplates bone fasteners, such as bone screws 12*a*-12*e*, having a lengthened intermediate portion between the bone-engaging threads and the rod-receiving tulip portion, as shown in FIG. 4. It can be appreciated from FIG. 4 that the cranial side screw 12*a* in the fixation construct can be conventional bone screws that are threaded into the bone with the rod-interface portion abutting the surface of the bone. However, the bone screws 12*b*-12*d* engaged to the lower lumbar vertebrae exhibit an increasing height from the threaded shank and the rod-engaging portion. In order to address this height differential, the present disclosure contemplates a bone screw 12 shown in FIG. 5. The bone screw 12 includes a shank 20 with bone-engaging threads, and an intermediate portion 18 that terminates in a tulip portion 14 that defines a U-shaped channel 14*a* to receive the rod. The end of the tulip portion 14 can be threaded to receive a conventional set screw 16 or other set screw construct suitable for clamping the spinal rod within the channel 14*a*. The bone screw 12 is configured to be threaded into vertebral bone until the base 15 of the intermediate portion 18 contacts the surface of the bone. In one aspect of the present disclosure, the bottom of the channel 14*a* is situated at a height H from the base 15 of the intermediate portion 18, as measured along the longitudinal axis L of the shank 20. This height H varies depending upon the position of the bone screw in the construct. Thus, as shown in construct depicted in FIG. 4, the height H is greater in screw 12*d* than screw 12*c*, and the height of screw 12*c* is greater than the height of screw 12*b*. In one aspect of the present disclosure, the bone screws can have intermediate portions 18 provided in a range of discrete heights, such as ranging from 0.5 mm to 30 mm in 0.5 mm increments.

The selection of the bone screws is preferably made in the planning stage, and most preferably using software operable to evaluate X-rays, CT scans and other advanced imaging techniques capable of accurately displaying the patient's spinal anatomy, in order to determine an optimum spinal construct. The software can assist in determining the spinal curvature, an acceptable curvature of the spinal rod for simplified introduction, and ultimately the amount of offset at each level of instrumentation—i.e., the gap between the reduced curvature rod and the desired position of the spinal level. The software can then assist in selecting the bone screw with the optimum height H for each level. The goal of this screw selection is that the tulip 14 of each bone screw is exactly aligned along the path of introduction of the reduced curvature spinal rod 10' so that the rod is solidly seated within each tulip by the time the rod reaches its caudal extent during percutaneous insertion. With this feature of the bone screws, the entire construct can be designed prior to the surgery, with the curvature of the rod being defined in the planning stage. The rod can then be pre-bent or pre-formed, as described above, and provided with a pre-determined collection of bone screws 10'.

The tulip portion 14 of the bone screw can be of any desired configuration, including fixed, uni-planar and poly-axial. The intermediate portion 18 can be uniform with the outer dimensions of the tulip portion along the extended height H and can merge into the threaded shank 20 in a conventional manner for bone screws, thereby preserving the structural integrity of the bone screw.

Figure 6:
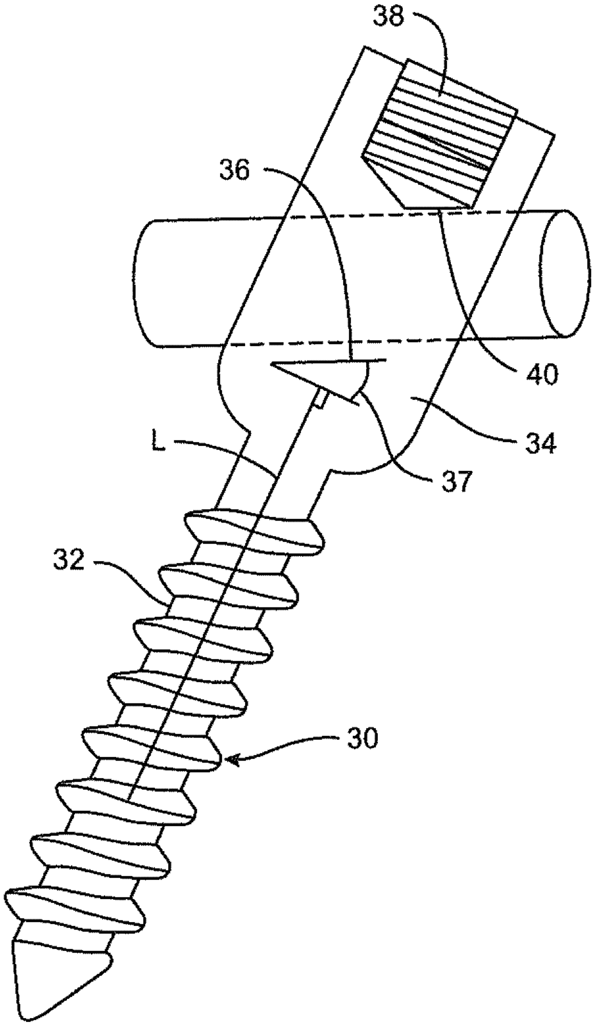
FIG. 6 is a view of a bone screw according to another aspect of the present disclosure.

In another feature of the present disclosure, a bone screw is provided that optimally creates a pre-defined sagittal relationship between the bone screw and the fixation rod. As described above, the rod 10' of the present disclosure has a fixed pre-determined curved contour that is configured for optimal correction of a patient's spinal deformity. Since the rod has a fixed contour, the interface between the rod and a particular vertebral body may not lend itself to the strict perpendicular interface required by prior fixed bone screws. In prior spinal constructs, poly-axial screws have been provided to address this angular misalignment, albeit at the cost of coronal correction. According to one aspect of the present disclosure, a bone screw 30 is provided as shown in FIG. 6. The bone screw 30 includes a threaded shank 32 and a tulip portion 34. A typical tulip portion of a bone screw includes a partially circular or U-shaped channel (such as channel 14*a* in FIG. 5), in which the channel extends along a line that is perpendicular to the longitudinal axis of the threaded shank. In one aspect of the present disclosure, the channel 36 of the tulip portion 34 is oriented at a non-perpendicular angle 37 relative to the longitudinal axis L of the threaded shank 32. More particularly, the angle 37 is measured relative to a line that is perpendicular to the longitudinal axis. A set screw 38, or suitable set screw construct, is threaded into the tulip portion 34 to clamp the spinal rod within the channel 36. In one aspect of the present disclosure, the set screw includes a tip 40 that is conical and defined at the same angle 37 relative to the longitudinal axis of the set screw. The combination of the angled channel 36 and the angled set screw tip 40 ensures a solid contact and fixation of the spinal rod traversing the tulip portion at an angle. The bone screw 30 can thus be a fixed screw, at least in the sagittal plane, in order to mate with a rod that is at an angle relative to the particular vertebral level. Several bone screws can be provided with channels 36 at pre-defined angles 37, such as between 5° and 45° in 5° increments.

The angled channel feature of the screw 30 can be integrated into an enhanced height screw, such as the screws 12*b*-12*e* described above. It can be appreciated that range of angles can be more limited for bone screws having a greater height H since the angular orientation of the rod relative the vertebral body would be less dramatic where the rod is farther away from the true curvature of the patient's anatomy.

As with the variable height feature of the bone screws, the angle of the channel 36 can be determined in the pre-operative planning. Once the shape of the fixation rod and the location of the bone screws is known, the desired angle of the rod relative to the bone screw at each vertebral level can be determined. The planning software can thus assist in the selection of the bone screw having the optimum height H and optimum angle of the channel 36. The planning software can also assist in optimization of both height and angle to control lordosis or kyphosis in a fusion construct. Providing a bone screw with an optimum sagittal angle allows the screw to be introduced at a precise predetermined optimum angle with respect to vertebral body or endplates. Subtly adjusting the angle between the pedicle screws and vertebra allows for fine tuning of the spinal alignment. This is an important feature of precise control of sagittal alignment with pedicle screws that is not possible with the prior art technique of placing screws at an uncontrolled angle.

Figure 7:
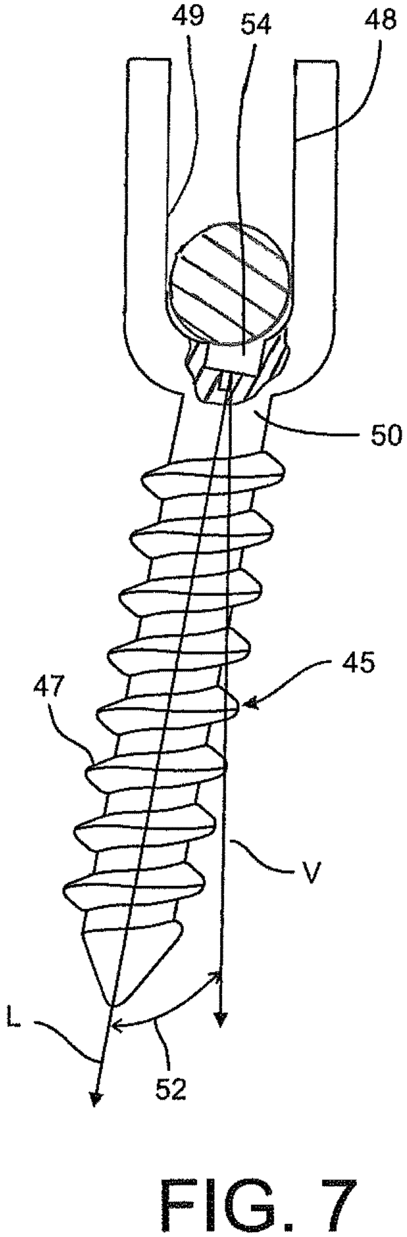
FIG. 7 is a view of a bone screw according to a further aspect of the present disclosure.

In another embodiment, a screw 45, shown in FIG. 7, includes a threaded shank 47 that is arranged at an angle 52 relative to the rod-engaging portion 48. The rod-engaging portion 48 may be in the form of a tulip, as described above, or another suitable feature capable of rod fixation. The rod-engaging portion 48 defines a channel 49 similar to the channel 14*a* in that the channel is perpendicular to the vertical axis V of the rod-engaging portion, as is known in the art. The rod-engaging portion is also configured to receive a conventional set screw or set screw construct for clamping the rod within the channel, such as the set screw 16 in FIG. 5. The interface 50 between the tulip 48 and the threaded shank 47 defines the angle 52. In particular, the threaded shank 47 defines a longitudinal axis L that is not colinear with the vertical axis V through the rod-engaging portion 48, and more particularly oriented at the angle 52. As with the typical bone screw, an insertion tool interface 54 is provided that can be engaged by a tool to thread the screw 45 into the vertebral bone in a known manner. However, unlike the conventional tool interface, the interface 54 is provided at the angle 52 relative to the longitudinal axis extending through the tulip 48. The tool is thus aligned with the threaded shank 47 for proper introduction of the screw into the bone. The tulip 48 can be otherwise configured as a conventional tulip rod-engaging portion. As with the bone screw 30 of FIG. 6, the bone screw 45 of FIG. 7 can be provided with pre-defined angles 52, such as between 5° and 45° in 5° increments. The angled shank 47 can be likewise integrated into an enhanced height screw, such as the screws 12*b*-12*e* described above.

It is contemplated that the bone screws 30, 45 accommodate angular deviations between the rod-engaging portion and the rod from the conventional perpendicular orientation. More specifically, the angular deviations are in the sagittal plane to accommodate the tulip configuration of the rod-engaging portions 34, 48. These "sagittally-biased" screws can be provided in several standard angles to account for the majority of spinal deformities. In contrast to conventional poly-axial screws, the screws of the present disclosure are rigid which facilitates sagittal alignment of the spine as the screws are tightened onto the contoured rod. Thus, the spinal construct disclosed herein achieves both coronal and sagittal correction of the spine in a minimally-invasive percutaneous procedure.

It should be understood that the bone screws disclosed herein can be used in a wide range of spinal constructs. For instance, the screws 12*b*-12*e*, 30 or 45 may be beneficial in a shorter construct with shorter rods. The same planning process can be used to assign a proper curvature to the shorter rod and to select the bone screws having the necessary height H, angled channel 36 and/or angled shank 47. These bone screws can be used with any shaped rod—straight or curved.

One differentiating feature of the rod 10' and bone screws 12*b*-12*e*, 30 or 45 is that the planning to achieve alignment of the spine is based on knowing the exact geometry of the rod ahead of time and using this known rod geometry as the foundation of the spinal alignment. This approach also allows selecting the appropriate bone screws ahead of time, secure in the knowledge that if the screws are implanted according to the predetermined plan the reduced curvature rod 10' can be easily introduced percutaneously into all of the rod-engaging portions of the bone screws. For instance, in a method for treating degenerative lumbar fusions, the pedicle screws of the present disclosure can be placed with a defined orientation relative to the vertebral endplates and with a pre-planned degree of bias. The rod can be passed percutaneously beneath the soft tissue and navigated into the tulips of the pedicle screws. Tightening the set screws corrects the spine to the desired segmental lordosis. As needed, the screws can "walk" along the rod to move the axis of rotation anteriorly prior to tightening.

The implant procedure starts with modeling the patient's spine using known software. A model of the modified rod disclosed herein is overlaid onto the spine model. As explained above, the rod has a fixed contour that is configured to facilitate percutaneous placement. The rod contour can be determined based on the dimensions of the patient's spine, as described above. The rod model is aligned with the spine model to achieve the desired correction, with the understanding that the excursion or offset from the rod to a particular vertebral body will vary along the length of the rod. Models of the bone screws are overlaid onto the models of the spine and rod, bridging the space between rod and spine and oriented at an optimum sagittal angle for proper fixation within the bone. The height from the rod to the bone surface and the angle of the threaded shank relative to the rod are determined and this information is used to select a bone screw modified as disclosed herein. The selected bone screws are precisely placed in the spine with the rod-engaging portion, or tulip, exactly aligned to accept the fixed contour rod. The rod is passed percutaneously into the aligned tulips and tightened onto the bone screws in a conventional manner.

It is contemplated that the rod 10' and the bone screws 12, 30 and 45 described herein are formed of medical grade materials suitable for use in spinal implant constructs. The rod and bone screws can be manufacture in a conventional manner for the fabrication of spinal implants.

The present disclosure should be considered as illustrative and not restrictive in character. It is understood that only certain embodiments have been presented and that all changes, modifications and further applications that come within the spirit of the disclosure are desired to be protected.

What is claimed is:

1. A method for forming a spinal construct for correcting a plurality of vertebral levels of a patient's spine, comprising the steps of:

determining the T10-S2 distance between the T10 vertebra and the S2 vertebra of the patient's spine;

determining the L1-S2 distance between the L1 vertebra and the S2 vertebra of the patient's spine;

providing a spinal rod having a total length at least equal to the T10-S2 distance, in which the spinal rod includes a caudal portion and a cranial portion, in which the length of the caudal portion is sixty percent (60%) of the total length and in which the caudal and cranial portions are oppositely curved at the same fixed radius to form a fixed curved contour of the spinal rod, wherein the fixed radius is calculated using the following equation—$((\text{L1}-\text{S2 distance})^2/8\text{ A})+\text{A}/2$, where A is the anterior displacement of the caudal portion, measured from a line between one end of the spinal rod and the cranial portion, that is 9-11% of the total length of the spinal rod;

providing a plurality of bone screws, each having:

an elongated shank having bone engaging threads and defining a longitudinal axis;

a rod-engaging portion defining a channel for receiving the spinal rod therein oriented perpendicular to said vertical axis; and an intermediate portion disposed between and directly connected to said rod-engaging portion and said elongated shank, said intermediate portion having a height along said longitudinal axis, wherein each of the plurality of bone screws has a different height ranging from 0.5 mm to 30 mm in 0.5 mm increments;

determining the distance between the caudal portion of the spinal rod and each of the instrumented L1-S1 vertebrae, and the distance between the cranial portion of the spinal rod and each of the instrumented T10-T12 of the patient's spine;

selecting one of the plurality of bone screws for each of the instrumented vertebrae having a height corresponding to the distance between the spinal rod and the corresponding vertebra;

implanting the selected bone screws into the corresponding vertebra; and attaching each of the selected bone screws to the spinal rod.

2. The method of claim 1, wherein the spinal rod and bone screws are introduced percutaneously.

* * * * *